United States Patent [19]
Jensen et al.

[11] Patent Number: 5,186,900
[45] Date of Patent: * Feb. 16, 1993

[54] BLOOD COLLECTION AND TRANSPORTATION ASSEMBLY FOR EVIDENTIARY PURPOSES

[75] Inventors: Richard E. Jensen, St. Peter; Donald H. Nichols, Roseville; D. Gary Hemphill, Wayzata, all of Minn.

[73] Assignee: Forensic Applications Corporation, Minneapolis, Minn.

[*] Notice: The portion of the term of this patent subsequent to Oct. 10, 2006 has been disclaimed.

[21] Appl. No.: 413,493

[22] Filed: Sep. 27, 1989

Related U.S. Application Data

[63] Continuation-in-part of Ser. No. 89,586, Aug. 26, 1987, Pat. No. 4,873,193, and a continuation-in-part of Ser. No. 212,016, Jun. 27, 1988, Pat. No. 4,917,867.

[51] Int. Cl.$^5$ .............................................. B01L 3/00
[52] U.S. Cl. .................................... 422/104; 422/61; 206/569; 206/570; 206/571
[58] Field of Search ............... 422/104, 61; 206/569, 206/570, 571, 497; 428/34.1, 34.9

[56] References Cited

U.S. PATENT DOCUMENTS

| | | | |
|---|---|---|---|
| 136,808 | 3/1873 | Beck | 206/570 |
| 985,850 | 3/1911 | Smith | 206/807 |
| 1,996,682 | 4/1935 | O'Brien | 206/807 |
| 2,410,928 | 11/1946 | Christner et al. | 206/569 |
| 3,849,256 | 11/1974 | Linder | 435/301 |
| 3,856,199 | 12/1974 | Gartz | 229/93 |
| 3,883,745 | 5/1975 | Glasser | 422/102 |
| 4,087,018 | 5/1978 | Tebbutt | 220/257 |
| 4,094,641 | 6/1978 | Friswell | 436/180 |
| 4,240,547 | 12/1980 | Taylor | 206/204 |
| 4,262,814 | 4/1981 | Roccaforte | 215/232 |
| 4,306,653 | 12/1981 | Falis | 206/497 |
| 4,362,698 | 12/1982 | Boosalis et al. | 422/102 |
| 4,418,702 | 12/1983 | Brown et al. | 422/101 |
| 4,446,970 | 5/1984 | Fürther | 206/571 |
| 4,564,299 | 1/1986 | Ehrenkranz | 374/157 |
| 4,769,215 | 9/1988 | Ehrenkranz | 422/58 |
| 4,832,046 | 5/1989 | Parrish | 128/771 |
| 4,886,071 | 12/1989 | Mehl et al. | 206/569 |
| 4,894,265 | 1/1990 | Chang et al. | 428/34.9 |
| 4,917,867 | 4/1990 | Jensen et al. | 422/102 |

Primary Examiner—Robert J. Warden
Assistant Examiner—Laura E. Collins
Attorney, Agent, or Firm—Moore & Hansen

[57] ABSTRACT

An assembly for collecting and transporting fluid biological samples such as blood including an impact resistant outer container having a soft foam cushioning pad disposed across the bottom and top thereof, a protective wrap of plastic bubble packaging material surrounding a pair of blood sampling tubes and a multi-sample syringe assembly disposed between the cushioning pads, a sealable evidence bag, tamper evidencing tapes, an instruction manual, a non-alcoholic swab, and an liquid absorbent packet contained therein. The outer container and its contents are initially enclosed and sealed in a tamper evidencing wrapper. The assembly may be subjected to extraordinarily rough handling with the contents of the blood sampling tubes remaining intact.

14 Claims, 3 Drawing Sheets

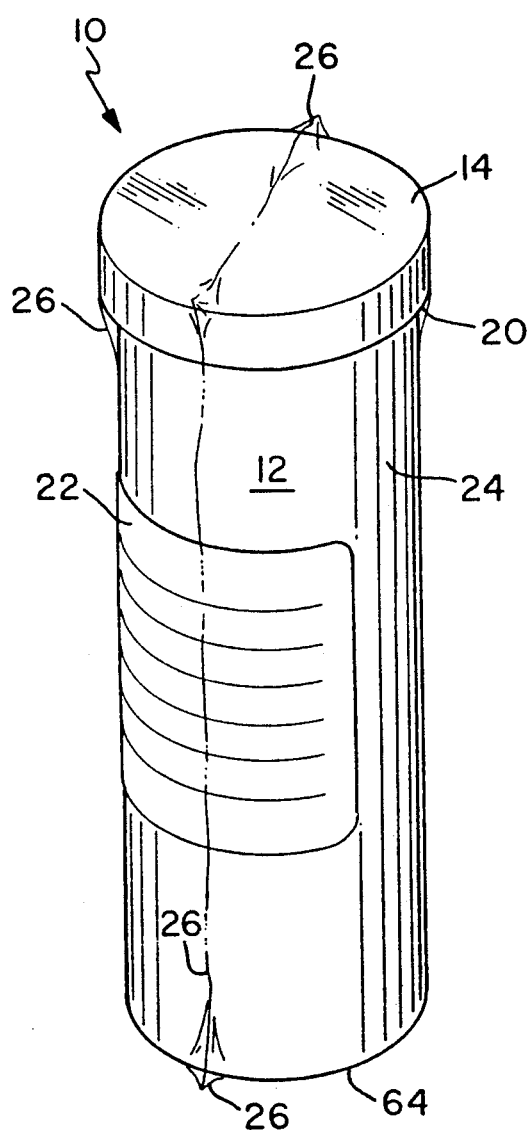
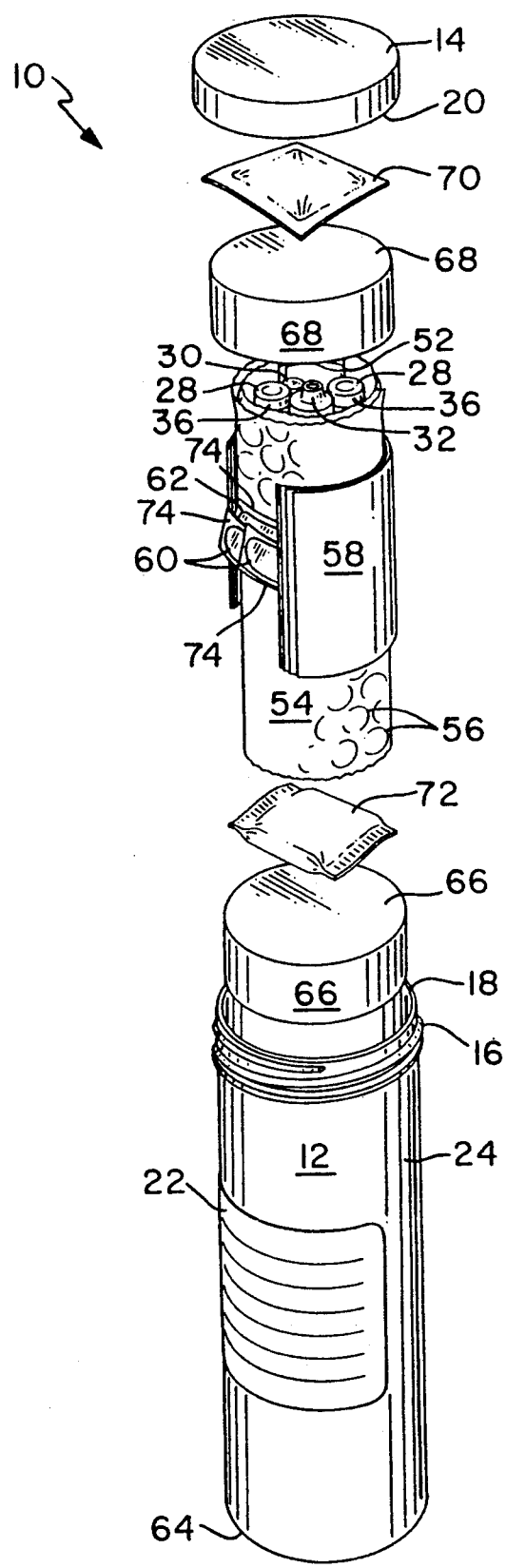
FIG. 1
FIG. 2

BLOOD COLLECTION AND TRANSPORTATION ASSEMBLY FOR EVIDENTIARY PURPOSES

This application is a continuation-in-part of pending U.S. patent application Ser. No. 07/089,586 filed on Aug. 26, 1987 now U.S. Pat. No. 4,873,193 and Ser. No. 07/212,016 filed on Jun. 27, 1988 now U.S. Pat. No. 4,917,867.

BACKGROUND OF THE INVENTION

This invention relates generally to an apparatus for collecting and transporting biological samples, and particularly to a field kit for use in taking multiple blood samples and capable of protecting those samples while being transported to a remote analytical laboratory.

The practical and evidentiary concerns associated with the design of devices for collecting and transporting biological samples are outlined in the co-pending U.S. Pat. applications identified above, and particularly Ser. No. 7/089,586, which relates to an apparatus for collecting and transporting dual biological specimens such as urine and blood.

The drawbacks and disadvantages associated with devices known to the prior art for collecting and transporting biological samples have been outlined and discussed in the above identified applications, as well as the responses and remarks submitted during the prosecution of those applications, which are incorporated herein by reference. While the various embodiments of the apparatuses disclosed in those applications provide effective solutions for many of the problems related to collecting and transporting samples, there are situations in which they do not provide the optimal selection to meet the needs of the persons performing or organizations supervising the collection or testing procedures.

One alternative which may be desired in certain situations is a system for use solely in collecting and transporting blood samples.

BRIEF SUMMARY OF THE INVENTION

It is therefore one object of this invention to design an evidentiary collection assembly specifically for collecting and transporting blood samples for use in analytical testing.

It is a further object of this invention to design the above assembly so as to be tamper-resistant or to evidence tampering, and to preserve a continuous evidentiary chain.

It is a related object of this invention to design the above assembly for use in as uniform, automatic, reliable, and reproducible a manner as possible.

It is an additional object of this invention to design the above assembly so as to be extremely durable, and to preserve the integrity of the sample and sample tubes even though the assembly may be subjected to physical shocks or adverse conditions.

Briefly described, the assembly of this invention for collecting and transporting fluid biological samples such as blood comprises an impact resistant outer container having a soft foam cushioning pad disposed across the bottom and top thereof, a protective wrap of plastic bubble packaging material surrounding a pair of blood sampling tubes and a multi-sample syringe assembly disposed between the cushioning pads, a sealable evidence bag, tamper evidencing tapes, an instruction manual, a non-alcoholic swab, and an liquid absorbent packet contained therein. The outer container and its contents are initially enclosed and sealed in a tamper evidencing wrapper. The assembly may be subjected to extraordinarily rough handling with the contents of the blood sampling tubes remaining intact.

BRIEF DESCRIPTION OF THE DRAWINGS

FIG. 1 is an perspective view of the assembly of this invention for transporting fluid biological samples such as blood shown in its initial condition;

FIG. 2 is an exploded perspective view of the assembly of FIG. 1 showing the outer container and its contents;

DESCRIPTION OF THE PREFERRED EMBODIMENT

Figure 3:
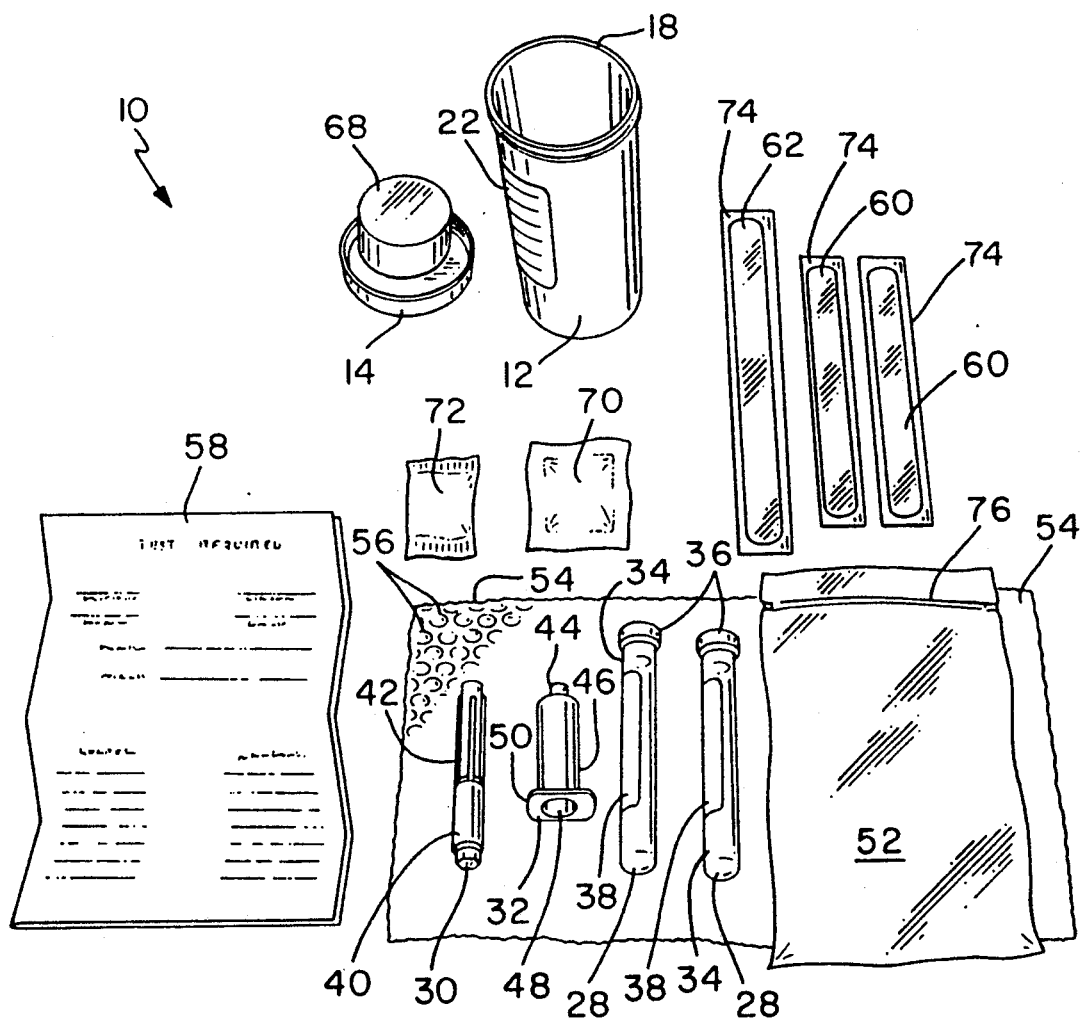
FIG. 3 is a perspective view of the assembly of FIG. 1 with the contents and outer container laid out for use.

The assembly of this invention for collecting and transporting fluid biological samples such as blood is shown in FIGS. 1-6 and referenced generally therein by the numeral 10.

Referring to FIGS. 1 and 2, it may be seen that the assembly 10 is contained within an outer container 12 having a generally cylindrical, plastic outer container body defining a receptacle region therein, and with a removable lid 14 having inner threads (not shown) aligned to engagingly mesh or seal with threads 16 along or below the rim 18 of the container 12. The outer container 12 and lid 14 are similar to that disclosed in the above referenced applications Ser. Nos. 07/089,586 and 07/212,016, however the receptacle region of the outer container 12 of this assembly 10 preferably has an inner height measured to the rim 18 of approximately 6 inches (or 15.25 cm.), and an internal radius of approximately 1-3/32 inches (or 2.75 cm.).

An adhesive mailing or routing label 22 is attached to the outer wall surface 24 of the outer container 12 having pertinent information such as the mailing address of an analytical testing laboratory or other predetermined destination printed thereon, or having the necessary space available for such information to be added. The outer container 12 and lid 14 should be molded from a resilient, highly impact resistant, opaque plastic resin, and is initially wrapped with a tamper resistant and tamper evident transparent shrink-wrapper 26.

Referring to FIGS. 2 and 3, it may be seen that slidably received within the outer container 12 are a pair of blood sampling tubes 28, a blood sampling syringe assembly 30, and a holder and protective guard 32 for the blood sampling tubes 28 and syringe assembly 30.

The blood sampling tubes 28, blood sampling syringe assembly 30 and holder and protective guard 32 may be of a type known to the art and available commercially through medical distributors, and have been described in detail in the above referenced application Ser. No. 07/212,016. Such suitable products are marketed under the name Vacutainer by Becton, Dickinson & Company of New Jersey, with representative examples of improvements and modifications in that product being shown in U.S. Pat. Nos. 4,317,456 and 4,436,098, and under the brand name MonoJect by Sherwood Medical of St. Louis, Missouri.

Each blood sampling tube 28 comprises a glass, sterile interior, round-bottomed test tube 34 having an open top and being sealed or closed at the circular rim thereof by a stopper 36 having a thin membrane covering and a thicker cylindrical side wall portion which depends into the top of the tube 28 and forms a sealing closure therewith. Each tube 28 is sterile and manufactured to produce a gentle vacuum therein, and may include a small aliquot of a dry preservative compound such as a 45 mg. mixture of potassium oxalate and sodium fluoride. An adhesive backed specimen identification label 38 is similarly attached to the outer surface of each tube 28, the label 38 having the appropriate printed information identifying the source of the tube 28, and suitable space for identifying the individual or entity supplying the blood sample contained therein.

The sterile, multi-sample blood sampling syringe assembly 30 is similarly described in the above referenced application Ser. No. 07/212,016, and consists of a long syringe needle or double ended cannula (not shown) defining a longitudinal bore and being mounted to and passing entirely through an intermediate retaining collar. The needle or cannula has a pair of opposing sharpened, bias cut ends, with one end of the needle projecting from the collar a distance greater than the opposing end. The shorter, opposing end is covered by a thin rubber protective sheath which is attached to the collar such that no portion of that end of the needle is exposed. The collar is molded from an impact resistant plastic and includes a plurality of threads on the side facing the shorter end of the needle. The long end of the needle is covered by a first protective cap or cover 40 which snaps over of frictionally engages a plurality of tines on the side of the collar opposing the threads, with the short end of the needle being covered by a second protective cap or cover 42 which snaps over and frictionally engages a recessed region of the first protective cap 40 to enclose the syringe needle.

As shown in FIG. 3, the holder and protective guard 32 is molded from an impact resistant plastic and includes a narrow neck 44 region defining a bore having internal threads corresponding to the threads on the collar of the blood sampling syringe assembly 30, a generally cylindrical body 46 defining an enclosed region 48 of sufficient size to accommodate the top of the sample tubes 28 including the stoppers 36, and an outwardly extending radial gripping collar 50 having opposing side extensions.

The second protective cap 42 may be removed from the shorter end of the syringe needle while gripping the first protective cap 40, and the threaded portion of the collar inserted into the bore of the holder and protective guard 32 and rotated to engage the threads of the collar and securely mount the syringe needle to the holder and protective guard 32. The holder and protective guard 32 is then placed over the top of one of the tubes 28 and pressed downward thereon, causing the shorter end of the needle to pierce the protective cover and the thin membrane in the stopper 36, and enter the interior region of the tube 28. The fingers of a person's hand may grip the outwardly extending radial gripping collar 50 by the opposing side extensions to exert a continuous pressure downwardly on the holder and protective guard 32 to maintain sealing contact with the tube 28. The first protective cap 40 may then be removed to expose the longer end of the needle, which may be inserted into a patient to extract a sample of blood. In this manner, the blood sampling tubes 28, blood sampling syringe assembly 30, and holder and protective guard 32 may be utilized to take one or more blood samples without requiring direct contact with the sampling needle and while maintaining as sterile a sample as is possible under normal conditions. The blood sampling tubes 28, blood sampling syringe assembly 30, and holder and protective guard 32 may then be disassembled by reversing this process, with the thin membranes of the blood sampling tubes 28 automatically closing over the puncture created by the short end of the needle to form a new sealing closure thereon.

As shown in FIGS. 2 and 3, the blood sampling tubes 28, blood sampling syringe assembly 30, protective guard 32, and a sealable plastic evidence bag 52 are grouped together and wrapped in a protective wrap 54 made from a generally rectangular sheet of shock resistant material, such as a bubble packaging material, made from polyethylene plastic sheets defining a multiplicity of enclosed air pockets 56 arranged in a single layer, spaced-apart or honeycombed array. The protective wrap 54 preferably has a width approximately equal to or less than the height of the receptacle region of the outer container 12, and a length of approximately one and a half times the circumference of the interior of the receptacle region of the outer container 12.

An instruction manual 58 having a chain of evidence record, and three sealing tapes 60, 62 are further wrapped around the blood sampling tubes 28, blood sampling syringe assembly 30, protective guard 32, sealable plastic evidence bag 52, and protective wrap 54, this bundle then being snugly received in the outer container 12.

This bundle is displaced from the bottom wall 64 of the outer container 12 by a first or lower cushioning pad 66 constructed from a disk of ⅞ths inch (2.25 cm.) thick open-cell urethane polyester foam having a density of approximately 2.0 PCF (or 0.032 gm/cm$^3$). A second or upper cushioning pad 68 of the same size and made of the same material is placed between the top of the protective wrap 54 and sample tubes 28 in the bundle and the interior of the lid 14. Both the lower and upper cushioning pads 66, 68 therefore have a generally resilient cushioning or shock absorbing property.

A microbicidal sterilizing swab 70 such as a prepackaged towlette containing a 10% iodine solution is placed on top of the second or upper cushioning pad 68. A desiccant material or liquid absorbent packet 72 having a soluble envelope containing approximately 3 grams of a vegetable polymer, such as described in U.S. Pat. Nos. 4,748,069 or 4,749,600, is disposed above the lower cushioning pad 66. The instruction manual 58 may be in leaflet or booklet form, with instructions for obtaining and preserving the evidence sample, handling the assembly 10 for transportation, and recording the chain of custody printed thereon. The instruction manual 58 should also contain a document upon which each intervening step in the collection and testing procedure may be recorded by the person undertaking that step of the procedure, so as to evidence and verify the chain of custody of the blood sampling tubes 28.

Figure 4:
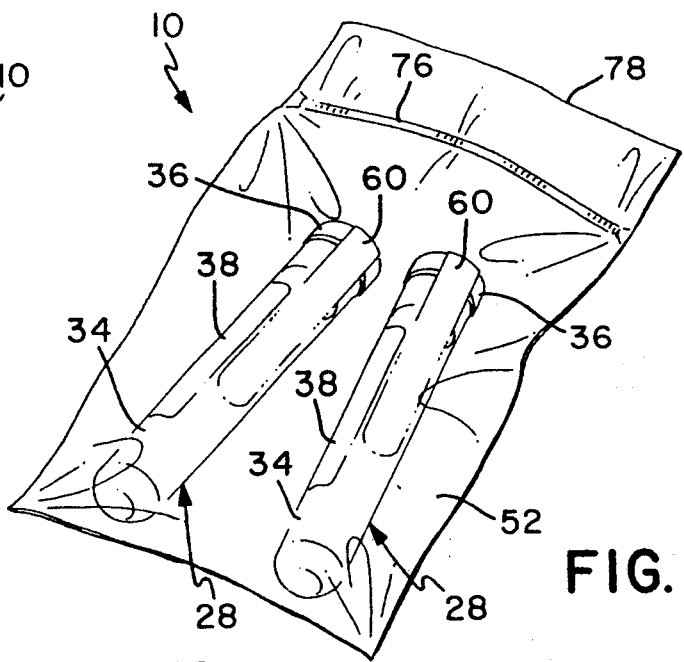
FIG. 4 is a perspective view of the components of the assembly of FIG. 1, particularly the sample tubes sealed within the evidence bag.
Figure 6:
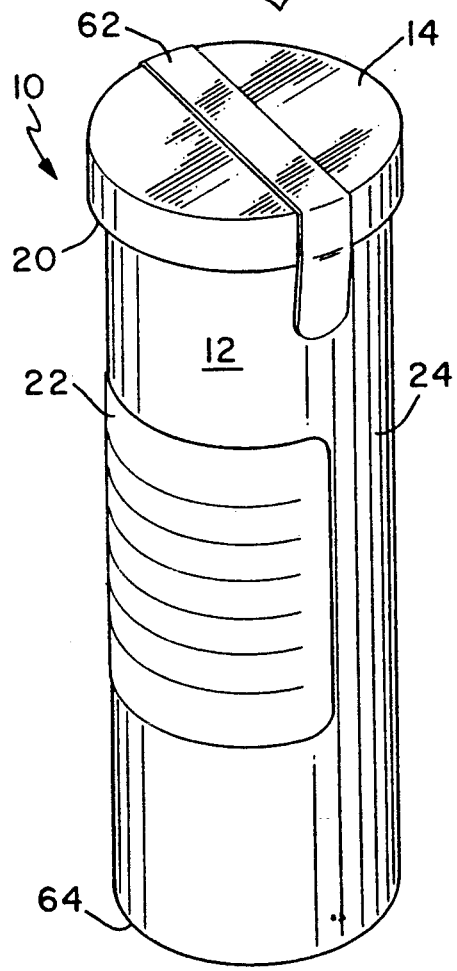
FIG. 6 is a perspective view of the resealed outer container of the assembly.

The sealing tapes 60, 62 each have an adhesive backing and are affixed to a non-adhering backing strip 74 from which they may be removed by peeling the length of the tapes 60, 62 away from and along the lengths of the strips 74. One pair of the tapes 60 has a shorter length and narrower width sufficient to extend across the stopper 36 of a sample tube 28 and downwardly on both sides of the tube 34 as shown in FIG. 4. One tape 62 has a greater width and a greater length sufficient to extend diagonally across the lid 14 of the outer container 12 and downwardly on both sides of the container 12, and a substantial distance downward along the outer surface of the container 12 as shown in FIG. 6. Each sealing tape 60, 62 is preferably constructed from a 32#paper with an adhesive coating which will not permit the tapes 60, 62 to be removed without visibly tearing or delaminating, and each tape 60, 62 should similarly have a printed safety pattern. The sealing tapes 60, 62 should extend along the opposing sides of the respective tube 34 or outer container 12 a substantial distance such that said sealing tapes 60, 62 cannot be removed without evidencing that removal.

Referring to FIGS. 3 and 4, it may be seen that the sealable plastic evidence bag 52 is generally rectangular and formed from two plies of general transparent or translucent plastic sheet material, having a two-part pressure sealable bead-type closure 76 proximate to the open top 78 thereof. The evidence bag 52 has a length and width sufficient such that the pair of the sampling tubes 28 may be completely enclosed within the bag 52 and the closure 76 sealed.

In operation, the person obtaining the sample will obtain the assembly 10 in the initial condition shown in FIG. 1, with the tamper-resistant outer wrapper 26 surrounding and sealingly enclosing the outer container 12 and lid 14 mounted thereon. The person will break the seal on and unwrap the assembly 10 from the tamper resistant outer wrapper 26, detach the lid 14 from the outer container 12, and remove the antiseptic swab 70, upper cushioning pad 68, and the bundle containing the instruction manual 58, sealing tapes 60, 62, blood sampling tubes 28, blood sampling syringe assembly 30, protective guard 32, sealable plastic evidence bag 52, and protective wrap 54. These contents, once removed from the outer container 12, may be unwrapped and set out as shown in FIG. 3.

Figure 5:
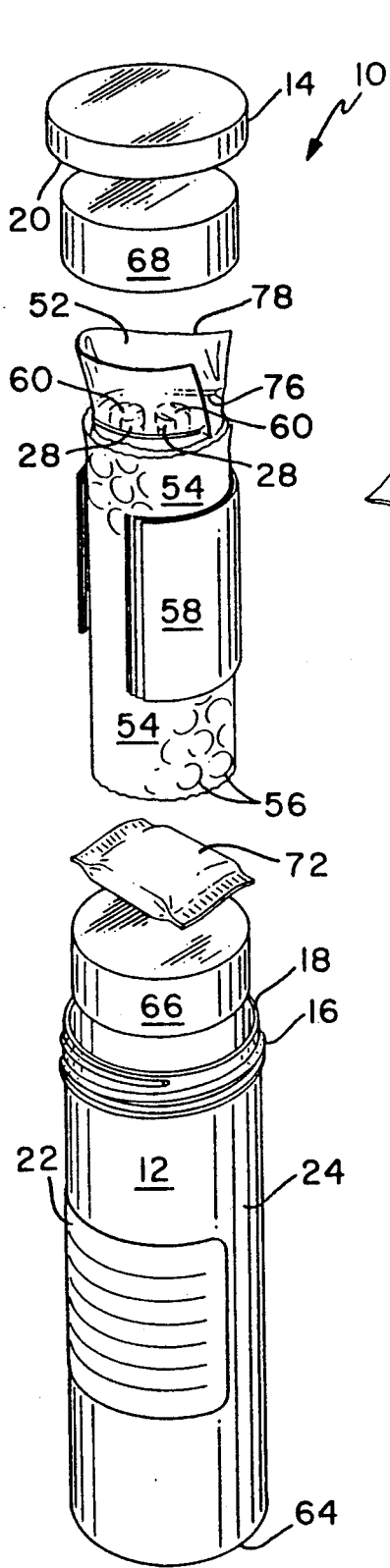
FIG. 5 is an exploded view showing the components of the assembly being reinserted into the outer container after a sample has been taken.

Following the instructions provided on the instruction manual 58, one or more samples of blood are taken using the blood sampling tubes 28, blood sampling syringe assembly 30, and holder and protective guard 32. One of the shorter sealing tapes 60 is applied to each of the blood sampling tubes 28 as described above, the pertinent identifying information recorded on the labels 38 of each sample tube 28, and the sample tubes 28 are then placed within the evidence bag 52 and the closure 76 sealed as shown in FIG. 4. These intervening steps are recorded on the document contained in the instruction manual 58 for verifying the chain of custody The sample tubes 28 in the evidence bag 52 are rewrapped in the protective wrap 54, and the instruction manual 58 is wrapped on the exterior of the protective wrap 54 as shown in FIG. 5. The lower cushioning pad 66 and liquid absorbent packet 72 are inserted into the receptacle region of the outer container 12, and will be pressed to the bottom 64 thereof as the sample tubes 28, evidence bag 52, and protective wrap 54 are inserted into and received completely within the receptacle region of the outer container 12. The upper cushioning pad 68 is then placed above the sample tubes 28 and protective wrap 54, and the lid 14 is firmly remounted on the top rim 18 of the outer container 12 covering the receptacle region.

The longer sealing tape 62 is peeled from the backing strip 74 and applied to the lid 14 and outer container 12 as shown in FIG. 6. Any necessary information concerning the individual supplying or the person collecting the fluid sample is recorded on the specimen label 22, and the assembly 10 may then be transported by any suitable carrier to a laboratory for analytical testing.

For analysis, the technician removes the sealing tape 62 from the outer container 12, removes the lid 14, upper cushioning pad 68, protective wrap 54, and sample tubes 28. The sample tubes 28 are removed from the evidence bag 52 and visually inspected to make sure the contents are complete and sealing tapes 60 intact. The blood sample tubes 28 may then be placed in a rack or holder (not shown) for use during the analysis, and samples extracted through the stoppers 36 using a suitable syringe or pipetting device.

In some instances, it may be preferable to mark evidentiary information directly on the evidence bag 52 with a permanent marker. It is also understood that a sealing tape could be used to seal the evidence bag 52, or the sealing tapes 60 made wide enough and applied so as to cover the entire top of the stoppers 36 since those stoppers 36 can be pierced undetectably using a hypodermic syringe, but it is deemed preferable to utilize a separate sealing tape 62 to evidence tampering of the outer container 12 at any time after sampling tubes 28 have been placed in the outer container 12 since the person using the assembly 10 will be less apt to make an error and will require less concentration, and the technician opening the outer container 12 will be abe quickly and easily verify its integrity.

While the preferred embodiment of the above assembly 10 has been described in detail above with reference to the attached drawing Figures, it is understood that various changes and adaptations may be made in the assembly 10 without departing from the spirit and scope of the appended claims.

What is claimed is:

1. An assembly for the collection and transportation of a sample of a biological fluid such as blood for evidentiary purposes, said sample to be collected by a user and placed within said assembly for transportation to a remote location, said assembly comprising:
    an outer container defining a receptacle region, said outer container having a bottom portion and a lid member mountable on said outer container opposing said bottom portion thereof;
    at least one sample tube for removably receiving and containing the sample;
    a protective wrap, said protective wrap surrounding said sample tube, said sample tube and said protective wrap being received within said receptacle region of said outer container;
    lower cushioning means for cushioning said sample tube, said lower cushioning means being disposed between said bottom portion of said outer container and said sample tube;
    upper cushioning means for cushioning said sample tube, said upper cushioning means being disposed between said lid member of said outer container and said sampler tube; and
    tamper-evidencing wrapper means, said outer container and said sample tube being initially received within said tamper-evidencing wrapper means prior to the sample being collected by the user and placed within said sample tube.

2. The assembly of claim 1 wherein the protective wrap is constructed from a sheet of a shock resistant material and wrapped surrounding the sample tube.

3. The assembly of claim 2 wherein the shock resistant material is a plastic material defining a multiplicity of enclosed air pockets.

4. The assembly of claim 2 wherein the protective wrap has a generally rectangular shape.

5. The assembly of claim 4 wherein the outer container has a height and the sheet has a width, said width being generally equal to or less than said height.

6. The assembly of claim 1 wherein the receptacle region defines a generally cylindrical shape having a radius, and wherein said upper cushioning means and said lower cushioning means each comprise a generally circular disk of a compressible foam material, each said generally circular disk having a radius approximately equal to said radius of the receptacle region.

7. The assembly of claim 1 wherein the upper and lower cushioning means are formed from an open cell foam material.

8. The assembly of claim 7 wherein the open cell foam material is a urethane polyester.

9. The assembly of claim 1 wherein the sample tube is a blood sampling tube having an interior region, and wherein the assembly further includes a multi-sample syringe assembly comprising:
   a syringe needle having a removable cover for enclosing said syringe needle; and
   a protective guard, said protective guard having a partially enclosed region which may receive at least a portion of the sample tube, said protective guard further including means for engagingly receiving said syringe needle,
   whereby the syringe needle, removable cover, and protective guard are initially surrounded by the protective wrap and received within the receptacle region of the outer container.

10. The assembly of claim 1 wherein the number of sample tubes is two.

11. The assembly of claim 1 wherein the sample tube
   a glass test tube having a generally cylindrical body defining an open top; and
   a stopper mountable on said glass test tube to close said open top thereof, said stopper having a thin membrane portion aligned with said open top of said glass test tube.

12. An assembly for the collection and transportation of a sample of a biological fluid such as blood for evidentiary purposes, said sample to be collected by a user and placed within said assembly for transportation to a remote location, said assembly comprising:
   an outer container defining a receptacle region, said outer container having a bottom portion and a lid member mountable on said outer container opposing said bottom portion thereof;
   at least one sample tube for removably receiving and containing the sample;
   a protective wrap, said protective wrap surrounding said sample tube, said sample tube and said protective wrap being received within said receptacle region of said outer container;
   lower cushioning means for cushioning said sample tube, at least a portion of said lower cushioning means being disposed generally between said bottom portion of said outer container and said sample tube to prevent contact between said bottom portion of said outer container and said sample tube;
   upper cushioning means for cushioning said sample tube, at least a portion of said upper cushioning means being disposed generally between said lid member of said outer container and said sample tube to prevent contact between said lid member of said outer container and said sample tube; and
   tamper-evidencing wrapper means, said outer container and said sample tube being initially received within said tamper-evidencing wrapper means prior to the sample being collected by the user and placed within said sample tube.

13. The assembly of claim 12 wherein the upper cushioning means and the lower cushioning means are not fabricated integral with the protective wrap.

14. The assembly of claim 13 wherein the upper cushioning means and the lower cushioning means are each fabricated from a shock-resistant foam material.

* * * * *

UNITED STATES PATENT AND TRADEMARK OFFICE
CERTIFICATE OF CORRECTION

PATENT NO. : 5,186,900

DATED : February 16, 1993

INVENTOR(S) : Richard E. Jensen et al

It is certified that error appears in the above-identified patent and that said Letters Patent is hereby corrected as shown below:

In Column 6, Line 29, delete "abe" and insert --able--.

Col. 7, claim 11, line 38, after the word "tube" insert --comprises:--.

Signed and Sealed this

Eighteenth Day of January, 1994

Attest:

BRUCE LEHMAN

*Attesting Officer*  *Commissioner of Patents and Trademarks*